United States Patent [19]

Higuchi et al.

[11] Patent Number: 4,677,131
[45] Date of Patent: Jun. 30, 1987

[54] CYCLIC UREAS AS DERMAL PENETRATION ENHANCERS

[75] Inventors: Takeru Higuchi; Stefano A. Pogany, both of Lawrence, Kans.

[73] Assignee: Merck & Co., Inc., Rahway, N.J.

[21] Appl. No.: 793,816

[22] Filed: Nov. 1, 1985

[51] Int. Cl.<sup>4</sup> ................... A61K 31/415; C07D 233/30
[52] U.S. Cl. .................................... 514/392; 548/317; 604/289; 604/290; 128/1 R
[58] Field of Search .......................... 548/317; 514/392

[56] References Cited

U.S. PATENT DOCUMENTS 3,876,657  4/1975  Aelony et al. ..................... 548/317

OTHER PUBLICATIONS

Forrest, T. P., et al., CA 81:151762y.
Aelony, David, et al., CA 77:88393d.
Timmler, Helmut, CA 57:9860a.
Asta-Werke A.G. Chemische Fabrik, CA 63:11572d.

Primary Examiner—John M. Ford
Assistant Examiner—Robert C. Whittenbaugh
Attorney, Agent, or Firm—Manfred Polk; Michael C. Sudol, Jr.

[57] ABSTRACT

Certain novel cyclic ureas are disclosed herein as dermal penetration enhancers of drug absorption. Also disclosed herein are compositions, methods of treatment and processes for preparing said cyclic urea compounds.

10 Claims, No Drawings

CYCLIC UREAS AS DERMAL PENETRATION ENHANCERS

BACKGROUND OF THE INVENTION

The invention relates to novel cyclic urea compounds useful in enhancing drug absorption through the skin. More specifically, the invention relates to said urea compounds being useful as penetration enhancers in topical compositions comprising an effective amount of a therapeutic agent. Also, the invention relates to processes for preparing said novel compounds.

Although there has been a greatly expanded recent interest in percutaneous drug deliver, efforts in this direction have been limited by the fact that most drug substances are poorly absorbed through the skin. This situation has recently led to a number of programs directed towards development of agents which would behave as enhancers of dermal absorption. Out of these studies a number of potential absorption promoters have been identified. These include dimethyl sulfoxide (DMSO), dimethyl acetamide (DMA), some surface-active agents, 2-pyrrolidone, N,N-diethyl-m-toluamide (Deet) and Azone® (1-dodecylazacycloheptane-2-one). Although most of these candidates have been shown to be effective in increasing the rate of drug transfer across the skin, their use has been limited in that very few dermal preparations containing them have actually reached the marketplace. This has probably been due to the real or imagined fear of their use leading to some undesired localized damage to the skin or to systemic toxicity. Of this group, only Deet has had a significant history of being applied to the skin, but as an insect repellent, rather than, an absorption adjuvant.

In spite of the fact that so many compounds have been evaluated for their effect on enhancing dermal penetration of drugs, the mechanism of enhancement and the controlling of physicochemical properties are still not well understood. One property which has been reportedly mentioned is the hydrogen bonding abilities of the effective enhancers. The conclusion is based on the known effectiveness of hydrogen accepting agents such as DMSO and DMA as absorption promoters. Since these solvents are known as strong hydrogen bonding acceptors, their hydrogen bonding abilities were considered to relate to their effectiveness as dermal penetration enhancers.

SUMMARY OF THE INVENTION

The invention relates to novel cyclic urea derivatives that are useful as promoters of drug penetration through the skin. Accordingly, it is an object of the invention to provide pharmaceutical formulations comprising a drug and a cyclic urea derivative as a penetration enhancer which will allow delivery of said drug via the skin.

A further object of the invention is to provide methods for the preparation of said novel derivatives.

Another object of the invention is to provide pharmaceutical compositions for administering drugs via cyclic urea compounds which provide the following:

(a) to enhance the bioavailability of drugs administered topically by administering therewith a cyclic urea penetration enhancing agent, and (b) to provide a stable dosage form utilizing a novel class of urea derivatives penetration enhancing agents which when administered topically will provide an increased blood level of the therapeutic agent.

A still further object of the invention is to provide a cyclic urea promoter of topical drug absorptions in concentrations which do not alter the normal morphology of the mucosal cells.

These and other objects and advantages of the present invention will become apparent from the following description.

DETAILED DESCRIPTION OF THE INVENTION

The invention relates to novel cyclic urea derivatives which are useful as dermal penetration enhancers for delivery of topically administered drugs through the skin. The novel penetration enhancers of the invention may be best described as comprising a compound of the formulae:

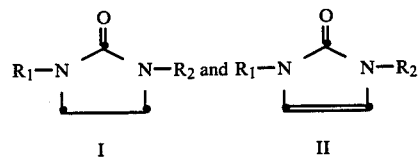

wherein $R_1$ and $R_2$ are independently hydrogen, aryl ($C_6$-$C_9$) such as phenyl, tolyl and the like; aralkyl ($C_7$-$C_{12}$) such as benzyl, phenethyl and the like; and alkyl ($C_1$-$C_{20}$) such as methyl, isopropyl, t-butyl, heptyl, decyl, dodecyl, tetradecyl, eicosyl and the like; with the proviso that when $R_1$ is hydrogen or alkyl ($C_1$-$C_5$), $R_2$ is not the same. This proviso does not apply to compositions, methods of treatment and processes inventions.

The compounds of Formulae (I) and (II) are generally prepared according to the reaction scheme described below by reacting a primary amine such as heptylamine, decylamine, benzylamine, aniline, phenethylamine, methylamine, hexyldecylamine, dodecylamine and the like, with an α-halodialkoxyacetaldehyde reagent such as α-chlorodimethoxyacetaldehyde, α-bromodiethoxyacetaldehyde and the like (1.1). The resultant secondary amine is reacted with an isocyanate (alkyl, aryl or aralkyl) reagent such as methylisocyanate, phenylisocyanate, benzylisocyanate and the like in the presence of an aliphatic or aromatic solvent such as benzene, xylene, heptane, iso-octane and the like to obtain a ureidoacetal (1.2) which is then acid cyclized (1.3) with a mineral acid such as hydrochloric, sulfuric, nitric and the like and stirred in the presence of an alkanol solvent such as methanol, isopropanol, t-butanol and the like for 1 to 3 days to give the compounds of Formula II. The compounds of Formula I are obtained via catalytic hydrogenation of the compounds of Formula II in the presence of an alkanol solvent such as methanol, ethanol, isopropanol and the like (1.4).

SYNTHESIS OF THE CYCLIC UREAS

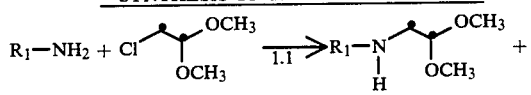

-continued
SYNTHESIS OF THE CYCLIC UREAS

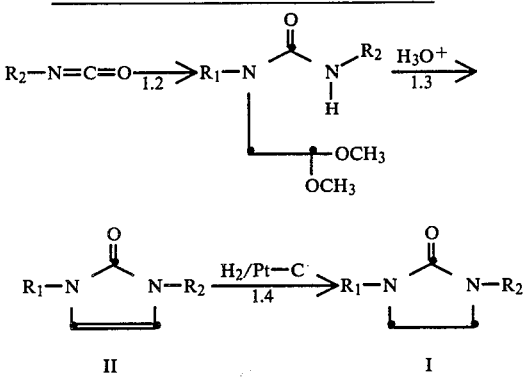

We have discovered that the cyclic urea derivatives of general Formulae (I) and (II) have the property of being able to promote dermal penetration of drug substances that are not by themselves capable of being sufficiently absorbed through the skin. Based on this information, the compounds of the instant invention are effective at doses of greater than or equal to 0.75 mg/dose. The compounds (I) and (II) have the added desirable characteristic of possessing no known pharmacological activity and of being non-damaging to the skin. Another important advantage of compounds (I) and (II) is the fact that, on a weight or dose basis, they are more active than other known absorption promoters (e.g., Azone® and DEET).

The preferred compounds of the present invention include the following:
1. 1-heptyl-3-methyl-2-imidazolidinone (Compound A),
2. 1-decyl3-methyl-2-imidazolidinone (Compound B),
3. 1-dodecyl-3-methyl-2-imidazolidinone (Compound C),
4. 1-heptyl-3-methyl-4-imidazolin-2-one (Compound D),
5. 1-decyl-3-methyl-4-imidazolin-2-one (Compound E), and
6. 1-dodecyl-3-methyl-4-imidazolin-2-one (Compound F).

The identity of the compounds was proved by spectral identification (NMR, IR). All compounds exhibited the correct elemental analysis.

Various active agents provide beneficial effects when administered to patients. Such agents which can be made more useful by enhancing its absorption in accordance with this invention, are exemplified by, but not limited to, the following classes of agents:

(1) β-Lactam antibiotics such as cefoxitin, N-formamidinylthienamycin, amoxicillin, ampicillin, azlocillin, bacampicillin, carbenicillin, cefaclor, cefadroxil, cefamandole, cefaparole, cefatrizine, cefazoline, cefonicid, cefaperazone, ceforanide, cefotaxime, cefotiam, cefroxadine, cefsulodin, ceftazidime, ceftizoxime, cephalaxin, cephaloglycin, cephaloridine, cephradine, cyclacillin, cloxacillin, dicloxacillin, floxacillin, hetacillin, methicillin, nafcillin, oxacillin, sarmoxacillin, sarpicillin, talampicillin, ticaricillin, penicillin G, penicillin V, pivampicillin, piperacillin, pirbenicillin and the like.

(2) Aminoglycoside antibiotics such as gentamycin, amikacin, astromicin, betamicin, butikacin, butirosin, clindamycin, josamycin, kanamycin, neomycin, netilmicin, tobramycin and the like.

(3) Antiviral and antineoplastic agents such as ara C (cytarabine), acyclovir, floxuridine, rabavirin, vidarabine, idoxuridine, trifluridine and the like.

(4) Amino acids such as methyldopa, carbidopa, levodopa, fludalamine and the like.

(5) Muscle relaxants such as theophylline, cyclobenzaprine, aminophylline, diphylline, oxtriphylline, ambuphylline, fenethylline, guathylline, pentoxyfylline, xanthinol niacinate, theophylline glycinate, glucophylline and the like.

(6) Polypeptides such as cyclo-(N-Me-Ala-Tyr-D-Trp-Lys-Val-Phe)acetate, somatostatin, insulin, gastrin, caerulein, cholecystokinin and the like.

(7) Anti-inflammatory agents such as indomethacin, sulindac, ibuprofen and the like.

(8) Diuretics such as aldactone, hydrochlorothiazide, amiloride, amiloride and hydrochloride and the like.

The enhancement of drug absorption in accordance with this invention is not by any means limited to the above drugs, but are in general applicable to other classes of drugs such as analgesics, anabolics, androgens, anorexics, adrenergics, antiadrenergics, antiallergics, antibacterials, anticholinergics, antidepressants, antidiabetics, antifungal agents, antihypertensives, antineoplastics, antipsychotics, sedatives, cardiovascular agents, antiulcer agents, anticoagulants, anthelmintics, radio-opaques, radio-nuclide diagnostic agents and the like.

The amount of drug varies over a wide range, but in general the therapeutically effective unit dosage amount of the selected drug depends on that amount known in the art to obtain the desired results.

Generally, the amount of adjuvant employed in the practice of this invention ranges from 0.75-100 mg in each unit dose. The percentage of adjuvant in the total combination of drug plus adjuvant is generally 5-99% with a preferred ratio of adjuvant in the total combination of adjuvant plus drug being 10-40%.

Some studies which further exemplified the invention are listed below:

A. In vitro Penetration Study

The rate of penetration of a drug, i.e. indomethacin and cyclic urea enhancers through shed snake skin and the full thickness rat skin was investigated using the apparatus and method described below. The amount of penetrants was analyzed by HPLC with RP-CN column.

Glass diffusion cells, having a short donor cell and long receptor cell, were prepared by using spherical O-ring joints, and were used for in vitro penetration studies through shed skin and silicone rubber membrane. The exposed membrane surface area in the diffusion cell measured 1.8 cm². Before being mounted to the diffusion cell, approximately 25 mg of ointment was carefully applied to the membrane and was spread over the desired area. The membrane was fixed with an O-ring between two sides and fastened tightly with a clamp. The receptor side was filled with approximately 8.5 ml of buffer solution consisting of $1.5 \times 10^{-1}$ M NaCl, $5.0 \times 10^{-4}$ M NaH$_2$PO$_4$, and $2.0 \times 10^{-4}$ M Na$_2$HPO$_4$ adjusted to pH 7.2 with sodium hydroxide. The diffusion cell was immersed vertically in a water bath in which the temperature was maintained at $32.0° \pm 0.1°$ C. The receptor cell was stirred constantly with a magnetic stirrer. To determine the amount of penetrating compounds, 0.2 ml samples were taken at varying time intervals from the receptor solution using a syringe inserted through a septum. An equal amount of fresh buffer was supplied through the septum during sampling.

B. Preparation of Ointment

Several 1% w/w indomethacin ointments each containing a different concentration of Urex or Urex-u were prepared by first dissolving indomethacin in the enhancer. The solution was then mixed with white petrolatum, USP, using a vortex mixer at around 55° C. The ointments were kept in a water bath at 32.0°±0.1° C. for 1 day before use for in vitro penetration studies. For the six individual cyclic ureas, five ointments each containing a different concentration of the enhancer were formulated. The values of five concentrations for each of the enhancers were the same for the six enhancers when expressed in terms of moles/Kg of the enhancer rather than % w/w. The relationship between moles/Kg and percentage of each enhancer in the formulation is represented in Table I.

TABLE I

Relationship Between % w/w and Moles/Kg of Cyclic Ureas in Formulation

| moles/Kg | % w/w enhancer | | | | |
|---|---|---|---|---|---|
| | 0.14 | 0.25 | 0.38 | 0.51 | 0.68 |
| Compound | | | | | |
| A | 2.7 | 4.9 | 7.5 | 10.1 | 13.4 |
| B | 3.3 | 6.0 | 9.1 | 12.3 | 16.3 |
| C | 3.6 | 6.7 | 10.2 | 13.7 | 18.2 |
| D | 2.7 | 4.9 | 7.4 | 10.0 | 13.3 |
| E | 3.2 | 5.9 | 9.0 | 12.2 | 16.1 |
| F | 3.6 | 6.6 | 10.1 | 13.6 | 18.0 |

C. Measurement of Partition Coefficient

The measurement of the partition coefficients of A thru F compounds as well as Azone ® between iso-octane and water was carried out by mixing iso-octane containing $5 \times 10^{-3}$ M of the enhancer with an equal volume of distilled water in a glass-stoppered bottle. The bottle was kept in a water bath at 32.0°±0.1° C., and the mixture was stirred constantly with a magnetic stirrer. After 24 hours, the concentration of the enhancer in both phases was determined by the HPLC method described in Table II. The partition coefficient of the enhancer was calculated from the data.

D. Acute Toxicity Study of C, F and Azone ® in Mouse

Female white Swiss mice weighing 20-30 g were used in this study. Mice were injected i.p. with an aqueous dispersion of C, F or Azone ® in 2% w/v polysorbate 80 in water. Control mice were injected with 2% w/v polysorbate 80 alone. The aqueous dispersions were prepared with the following enhancer concentrations: 1.8, 2.5, 3.5, 5.0, 7.1, 10 and 14.1 mg/ml. When these were administered i.p. at a volume of 1 ml/25 g mouse, the corresponding doses of the enhancer were 70, 100, 141, 200, 282, 400 and 565 mg/Kg.

The mice were observed for 7 days post-injection and the mice that died during this period of time were counted. The values of the acute $LD_{50}$ of enhancers were calculated based on the method of L. J. Reed, Amer. J. Hyg., 27:493 (1938).

TABLE II

| HPLC Conditions[1] for Analysis | | |
|---|---|---|
| Compound | Mobile phase | Detection wavelength, nm |
| Indomethacin | 40 v/v % acetonitrile-water containing 20 mM $NH_4H_2PO_4$ | 254 |
| A | 55 v/v % acetonitrile-water | 210 |
| B | 90 v/v % acetonitrile-water | 210 |
| C | 95 v/v % acetonitrile-water | 210 |
| $D^2$ | 40 v/v % acetonitrile-water | 254 |
| E | 90 v/v % acetonitrile-water | 214 |
| F | 95 v/v % acetonitrile-water | 214 |
| Azone ® | 95 v/v % acetonitrile-water | 210 |

[1]The column used for whole analysis was μBondapak CN-RP of Waters Associates.
[2]$D^2$ was simultaneously determined along with indomethacin when both compounds were needed.

E. Skin Irritation Study

Fuzzy rats, weighing around 250 g, were used to study the dermal irritancy of Compounds C and F as well as Azone ®. The agents were administered in the form of their 20% w/v ethanolic solution. Exactly 50 μl of the test solutions, containing 10 mg of an enhancer, were applied to circular gauze pads 1 mm thick and 16 mm in diameter, and affixed to the animals' dorsal surface with occlusive adhesive film. The occlusive dressings were removed after 3 days. Erythemal response (redness) was then evaluated for each site according to a modified Draize method and graded on a scale of 0–4 (4 being the response of maximum redness).

F. Effect of the Length of the Alkyl Side Chain on Melting Points and Partition Coefficients of Homologous Series of A–C and D–F compounds As shown in Table III, the melting point rose with an increase in the length of the alkyl side chain in both series of A–C and D–F compounds.

TABLE III

Melting Points of A–C and D–F Compounds

| | Melting point, °C. | |
|---|---|---|
| Number of alkyl side chain | A–C compounds | D–F compounds |
| 7 | below $-4^1$ | below $-4^1$ |
| 10 | $18^2$ | $36^2$ |
| 12 | $32^2$ | $52^2$ |

[1]These compounds were not solidified when stored at −4° C.
[2]Measured with differential scanning calorimetry (DSC), Perkin Elmer, type 4.

Partition coefficients also increased with an increase of the alkyl side chain number in both A–C and D–F series of compounds as shown in Table IV below.

TABLE IV

Partition Coefficient of A–C and D–F Compounds at 32° C.

| Compound | Partition coefficient[1] |
|---|---|
| A | 24 |
| B | 756 |
| C | 7350 |
| D | 3 |
| E | 165 |
| F | 2540 |
| Azone ® | 2004 |

[1]Partition coefficient between iso-octane and water.

G. Acute Toxicity in Mice and Skin Irritation on Fuzzy Rat of Compound C and Azone ®

The results of ane acute toxicity study in a mouse of Compound F and Azone ® are given in Table V. The calculated values of $LD_{50}$ indicate that Urex 12 is less toxic than Azone ®. At equal efficacy level the cyclic urea is significantly less toxic than Azone ®. For example, at the lower concentration of these enhancers in formulations, Compound C was approximately two times as effective as Azone ®. Thus at an equal efficacy level Compound C appears to be substantially less toxic than Azone ®. The results of the irritation study on fuzzy rats of these enhancers are shown in Table V. When 10 mg of each compound were applied to 2 cm² of skin, Compound C and Azone ® showed very slight erythema (redness).

TABLE V

Acute toxicity of Compound C and Azone ® in Mouse

| Dose[2], mg/Kg | Number of dead mice[1]/number of total mice | |
|---|---|---|
| | Compound C | Azone ® |
| 70 | — | — |
| 100 | — | 0/7 |
| 141 | — | 1/10 |
| 200 | — | 7/10 |
| 282 | 0/10 | 9/10 |
| 400 | 8/10 | 8/8 |
| 564 | 3/3 | — |
| LD$_{50}$, mg/Kg[3] | 435 | 232 |

[1]Number of mice that died within 7 days post-injection.
[2]The enhancers were given i.p. The vehicle was 2% w/v aqueous polysorbate 80.
[3]The values of LD$_{50}$ were calculated based on the method of Reed Ibid.

The results indicate that Urex 12 is a safer enhancer than Azone ® for use in the clinical stage. Based on the suggested utility of Azone ® for commercial preparations, it would appear that the cyclic ureas offer significant advantages as enhancers because of their greater activity and less toxicity.

The following examples illustrate preparation of various novel cyclic urea compounds and compositions of the invention. The examples should be construed as illustrations rather than limitations thereof.

EXAMPLE 1

Step 1.1: 1-Dodecyl-3-methyl-2-imidazolidinone

Dodecylamine (40 g, 0.216 moles) was combined with α-chloroacetaldehyde dimethyl acetal (27 g, 0.216 moles) without solvent and the mixture heated for eight hours at 120° C. The reaction was allowed to cool to 25° C. and added 300 ml of ethyl ether to dissolve product(s) and to precipitate the NaCl formed. The solids were removed by filtration. There was obtained 32.40 g of crude material as a brown liquid. Thin layer chromatography (10% methanol-dichloromethane) showed the appearance of a major spot that was identified (NMR) as α-dodecylaminoacetaldehyde dimethyl acetal. This material was used without purification in the next step.

When substituting other α-halodialkoxyacetaldehyde such as α-bromodiethoxyacetaldehyde for α-chlorodimethoxyacetaldehyde at an appropriate temperature, there is obtained the corresponding compound.

Step 1.2:

The aminoacetal from Step 1.1 (32.40 g, 0.118 moles) was dissolved in 200 ml of dry toluene and the solution was cooled to 0° C. in an ice bath. Methyl isocyanate (6.76 g, 0.118 mole) was added dropwise as a solution in 20 ml of dry toluene and the mixture was allowed to warm to 25° C. and was stirred at this temperature for 2 hours. Thin layer chromatography showed the appearance of a new spot that was identified (NMR) as the desired ureidoacetal. The solvent was evaporated to yield 29 g of a dark brown liquid that was used as such in Step 3.

When substituting other isocyanates such as phenylisocyanate or benzylisocyanate for methylisocyanate, there is obtained the corresponding compound.

Step 1.3:

The ureido-acetal from Step 1.2 (29 g) was dissolved in 500 ml of ethanol and 50 ml of 2N hydrochloric acid was added. The mixture was stirred at 25° C. for 2 days and the reaction monitored for completion by thin layer chromatography (30:30:30 ethyl acetate-acetone-dichloromethane). The reaction was neutralized with 2N sodium hydroxide and solid material was removed by filtration. The ethanol was evaporated and to the residue was added dichloromethane. One additional filtration removed material which did not dissolve in dichloromethane. After evaporation of the solvent there was obtained 6 g of crude 1-dodecyl-3-methyl-4-imidazolin-2-one corresponding to a compound of formula (II). The material was purified by column chromatography

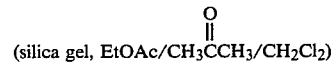
(silica gel, EtOAc/CH$_3$CCH$_3$/CH$_2$Cl$_2$)

and exhibited correct elemental analysis and NMR spectra.

When substituting other solvents such as methanol, t-butanol or isopropanol for ethanol and sulfuric acid or nitric acid for hydrochloric, there is obtained the corresponding compound.

Step 1.4:

1-Dodecyl-3-methyl-4-imidazolin-2-one from step 1.3), (8.83 g) was dissolved in 200 ml of EtOH and hydrogenated for 24 hours with 10% platinum on carbon as the catalyst to give in high purity as shown by TLC

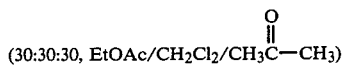
(30:30:30, EtOAc/CH$_2$Cl$_2$/CH$_3$C—CH$_3$)

the product 1-dodecyl-3-methyl-2-imidazolidinone. There was obtained 8.37 g of white, crystalline material with correct elemental analysis and NMR spectra.

When substituting other solvents such as methanol or isopropanol, there is obtained the respective product. The above 4-step synthesis of the dodecyl-methyl derivatives applies with minor variations (temperature, duration of reaction) to all compounds of formulas (I) and (II). This 4-step process is definitely superior to direct alkylation procedures of the pre-formed ring structures.

What is claimed is:

1. A pharmaceutical composition for enhancing absorption of a topically administered formulation comprising a therapeutically effective amount of a drug and a skin penetration enhancing agent of the formulae:

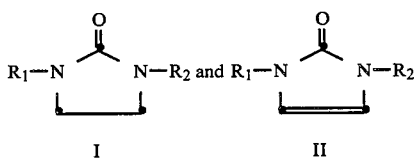

wherein R$_1$ and R$_2$ are independently hydrogen, aryl selected from the group consisting of phenyl and tolyl, aralkyl selected from the group consisting of benzyl and phenethyl or alkyl (C$_1$–C$_{20}$).

2. The composition of claim 1 wherein said drug is selected from the group consisting of β-lactam antibiotics, aminoglycosides, antineoplastic and antiviral agents, amino acids, muscle relaxants, polypeptides, anti-inflammatory agents and diuretics and the penetration enhancing agent is represented by formulae I and II wherein $R_1$ and $R_2$ is selected from the group consisting of alkyl and aralkyl.

3. The composition of claim 2 wherein said drug is an antibiotic selected from the group consisting of cefoxitin, penicillin G, penicillin, amoxicillin, N-formamidinylthienamycin, cefadroxil, gentamycin, neomycin, clindamycin, astromicin and betamicin; a polypeptide selected from the group consisting of gastrin, somatostatin, insulin and cyclo-(N-Me-Ala-Tyr-D-Trp-Lys-Val-Phe)acetate; an antineoplastic and antiviral agent selected from the group consisting of acyclovir, fluxuridine, ribovirin, cytarabine and vidarabine; an amino acid selected from the group consisting of methyldopa, levodopa and carbidopa; a muscle relaxant selected from the group consisting of cyclobenzaprine and theophylline; an anti-inflammatory agent selected from the group consisting of indomethacin and sulindac; and a diuretic selected from the group consisting of hydrochlorothiazide, amiloride and amiloride and hydrochlorothiazide.

4. The composition of claim 1 further comprising pharmaceutically acceptable excipients.

5. A method of enhancing the rate of dermal absorption of a topically administered composition comprising a therapeutically effective dosage amount of a drug and a skin penetration enhancing agent of the formulae:

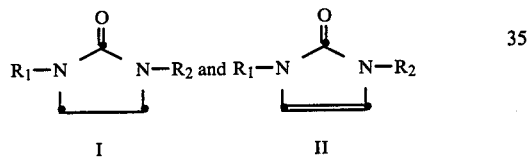

wherein $R_1$ and $R_2$ are independently hydrogen, aryl selected from the group consisting of phenyl and tolyl, aralkyl selected from the group consisting of benzyl and phenethyl or alkyl ($C_1$–$C_{20}$).

6. The method of claim 5, wherein the drug is selected from the group consisting of β-lactam antibiotics, aminoglycosides, antineoplastic and antiviral agents, amino acids, muscle relaxants, polypeptides, anti-inflammatory agents and diuretics and the penetration enhancing agent is represented by formulae I and II wherein $R_1$ and $R_2$ is selected from the group consisting of alkyl and aralkyl.

7. The method of claim 6, wherein the drug is an antibiotic selected from the group consisting of cefoxitin, penicillin G, penicillin, amoxicillin, N-formamidinylthienamycin, cefadroxil, gentamycin, neomycin, clindamycin, astromicin and betamicin; a polypeptide selected from the group consisting of gastrin, somatostatin, insulin and cyclo-(N-Me-Ala-Tyr-D-Trp-Lys-Val-Phe)acetate; an antineoplastic and antiviral agent selected from the group consisting of acyclovir, fluxuridine ribovirin, cytarabine and vidarabine; an amino acid selected from the group consisting of methyldopa, levodopa and carbidopa; a muscle relaxant selected from the group consisting of cyclobenzaprine and theophylline; an anti-inflammatory agent selected from the group consisting of indomethacin and sulindac; and a diuretic selected from the group consisting of hydrochlorothiazide, amiloride and amiloride and hydrochlorothiazide.

8. A process for preparing a compound of the formulae:

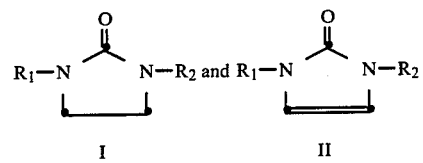

wherein $R_1$ and $R_2$ are independently hydrogen, aryl ($C_6$–$C_9$), aralkyl ($C_7$–$C_{12}$) or alkyl ($C_1$–$C_{20}$), which comprises the steps of (A) reacting a compound of the formula:

$R_1$—$NH_2$ with an α-halodialkoxyacetaldehyde at temperatures ranging from 100° C. to 130° C. to obtain a compound of the formula:

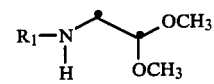

(B) treating the resulting secondary amine with an isocyanate reagent in the presence of an aliphatic or aromatic solvent at temperatures ranging from −10° C. to 35° C. to obtain a ureido-acetal compound of the formula:

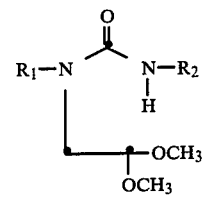

(C) cyclizing the ureido-acetal compounds in the presence of an alkanol solvent with a mineral acid to give the compounds of formula II below:

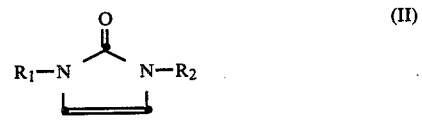

(D) catalytic hydrogenation of the compounds of step C in the presence of an alkanol solvent gives the compound of formula I below:

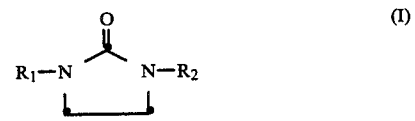

9. The process of claim 8, wherein:
(A) the α-halodialkoxyacetaldehyde is selected from the group consisting of α-chlorodimethoxyacetaldehyde and α-bromodiethoxyacetaldehyde, (B) the isocyanate reagent is selected from the group consisting of methylisocyanate, phenylisocyanate and benzylisocyanate,
(C) the acid is selected from the group consisting of hydrochloric, sulfuric and nitric and the solvent is selected from the group consisting of methanol, isopropanol and t-butanol, and
(D) the solvent is selected from the group consisting of methanol, ethanol, isopropanol and t-butanol.

10. The process of claim 9, wherein:
(A) the reagent is 60-chloroacetaldehyde,
(B) the reagent is methylisocyanate, and the solvent is toluene,
(C) the solvent is ethanol and the acid is hydrochloric, and
(D) the hydrogenation is carried out with ethanol as the solvent.

* * * * *